US008529063B2

(12) United States Patent
Bonnin et al.

(10) Patent No.: US 8,529,063 B2
(45) Date of Patent: Sep. 10, 2013

(54) OPHTHALMIC SPECTACLES FOR CHARACTERIZING A CONVERGENCE OF THE EYES OF A WEARER

(75) Inventors: Thierry Bonnin, Charenton le Pont (FR); Thibault Brossier, Charenton le Pont (FR); Benjamin Rousseau, Charenton le Pont (FR)

(73) Assignee: Essilor International (Compagnie Generale d'Optique), Charenton le Pont (FR)

( * ) Notice: Subject to any disclaimer, the term of this patent is extended or adjusted under 35 U.S.C. 154(b) by 123 days.

(21) Appl. No.: 13/320,008

(22) PCT Filed: May 7, 2010

(86) PCT No.: PCT/FR2010/050893
§ 371 (c)(1),
(2), (4) Date: Nov. 10, 2011

(87) PCT Pub. No.: WO2010/130931
PCT Pub. Date: Nov. 18, 2010

(65) Prior Publication Data
US 2012/0050681 A1    Mar. 1, 2012

(30) Foreign Application Priority Data
May 12, 2009   (FR) ...................................... 09 53126

(51) Int. Cl.
*A61B 3/14*    (2006.01)
*A61B 3/04*    (2006.01)
(52) U.S. Cl.
USPC ............................ 351/210; 351/209; 351/229

(58) Field of Classification Search
USPC .................................................. 351/200–246
See application file for complete search history.

(56) References Cited

U.S. PATENT DOCUMENTS

| 3,689,135 A | 9/1972 | Young et al. | 351/246 |
| 4,300,818 A | 11/1981 | Schachar | 351/210 |
| 5,070,883 A | 12/1991 | Kasahara | 600/553 |

(Continued)

FOREIGN PATENT DOCUMENTS

| EP | 0733338 A1 | 9/1996 |
| WO | 9918868 A1 | 4/1999 |

OTHER PUBLICATIONS

Reulen et al. "Precise recording of eye movement: the IRIS technique Part 1", *Med. & Biol. Eng. & Comput. 26*:20-26, 1988. 7 Pages.

(Continued)

*Primary Examiner* — Mohammed Hasan
(74) *Attorney, Agent, or Firm* — Seed IP Law Group PLLC

(57) ABSTRACT

The invention relates to ophthalmic spectacles for characterizing a convergence of the eyes of a wearer. Each lens of the spectacles is provided with output sections for guiding a radiation towards the side areas of an eye of the carrier, in which the right and left portions of the corneal margin of said eye are in motion. The lens further comprises input sections for collecting the portions of said radiation reflected in said side areas of the eye. A computing unit is also combined with the spectacles in order to determine the convergence of the eyes of the wearer from detection signals measuring the portions of the radiation that are simultaneously collected by the input sections of the two lenses.

17 Claims, 5 Drawing Sheets

(56) References Cited

U.S. PATENT DOCUMENTS

| | | | |
|---|---|---|---|
| 5,345,281 A * | 9/1994 | Taboada et al. | 351/210 |
| 5,668,622 A | 9/1997 | Charbonnier et al. | 351/209 |
| 5,966,197 A | 10/1999 | Yee | 351/209 |
| 6,283,954 B1 | 9/2001 | Yee | 606/5 |
| 6,299,307 B1 | 10/2001 | Oltean et al. | 3/1 |
| 7,815,311 B2 * | 10/2010 | Johns et al. | 351/209 |
| 8,025,405 B2 * | 9/2011 | Rehnstrom | 351/210 |
| 2011/0051082 A1 * | 3/2011 | Becken et al. | 351/177 |

OTHER PUBLICATIONS

"Applied Science Laboratories—Eye Tracking Expertise", Applied Science Laboratories, Copyright 2009. Retrieved Jul. 11, 2012. URL=http://www.a-s-l.com/, 1 Page.

"Eye Tracking Systems—HMD Mounted Eye Tracking Systems", Arrington Research, Inc. Retrieved Jul. 11, 2012. URL=http://www.arringtonresearch.com/headmountframe.html, 1 Page.

"Eyetrackers for eye movement research, analysis and evaluation", COGAIN: Communication by Gaze Interaction. Last modified Mar. 21, 2012. Retrieved Jul. 11, 2012. URL=http://www.cogain.org/eyetrackers/eyetrackers-for-eye-movement-research, 5 Pages.

"Cambridge Research Systems Ltd.—BOLDscreen for fMRI", Cambridge Research Systems Ltd., Copyright 2011. Retrieved Jul. 11, 2012. URL=http://www.crslid.com/catalog/mri-live/index.html, 2 Pages.

"Cambridge Research Systems Ltd.—High-Speed Video Eye Tracker Toolbox", Cambridge Research Systems Ltd., Copyright 2011. Retrieved Jul. 11, 2012. URL=http://www.crslid.com/catalog/calar/index.html, 2 Pages.

"Cambridge Research Systems Ltd.—Home", Cambridge Research Systems Ltd., Copyright 2011. Retrieved Jul. 11, 2012. URL=http://www.crsltd.com/catalog/mr-eyetracker/index.html, 2 Pages.

"EyeTech Digital Systems—Industry Leading Eye Tracking Solutions", EyeTech Digital Systems, Copyright 2010. Retrieved Jul. 11, 2012. URL=http://www.eyetechds.com/, 2 Pages.

"Fourward Technologies, Inc.—Home", Fourward Technologies, Inc. Last updated Jul. 2, 2010. Retrieved Jul. 11, 2012. URL=http://www.fourward.com/, 4 Pages.

"Eyegaze.com—Eye tracking that brings power to sight 800-393-429", LC Technologies, Inc., Copyright 2012. Retrieved Jul. 11, 2012. URL=http://www.eyegaze.com/, 2 Pages.

"Metrovision: instruments de mesure des fonctions visuelles", Metrovision. Retrieved Jul. 11, 2012. URL=http://www.metrovision.fr/index-fr.html, 4 Pages.

"Motion Imaging and Analysis-Motion Analysis Software and Hardware ; MIC Motion Imaging and", Motion Imaging Corp, Copyright 2006. Retrieved Jul. 11, 2012. URL=http://mi-as.com/products/eye-tracking/#emr-8b, 4 Pages.

"ExpressEye", Optomotor Laboratory, Copyright 1997. Retrieved Jul. 11, 2012. URL=http://www.optom.de/english/exe.htm, 2 Pages.

"Eye Tracking System CS681", Primelec, D. Florin. Retrieved Jul. 11, 2012. URL=http://www.primelec.ch/cs681/cs681.htm, 5 Pages.

"Smarteye | If you want reality", Smart Eye AB. Retrieved Jul. 11, 2012. URL=http://www.smarteye.se/, 1 Page.

"Eyetracking and Eye Tracker | Sensomotoric Instruments (SMI)", SensoMotoric Instruments GmbH. Retrieved Jul. 11, 2012. URL=http://www.smi.de/home/index.html, 1 Page.

"Eye Tracking Systems", Thomas RECORDING GmbH, Copyright 2002. Retrieved Jul. 11, 2012. URL=http://www.thomasrecording.de/en/cms/front_content.php?idcatart=63 &lang=1&client=1 , 2 Pages.

"Eye tracking and eye control for research, communication and integration", Tobii Technology, Copyright 2011. Retrieved Jul. 11, 2012. URL=http://www.tobii.com/, 1 Page.

* cited by examiner

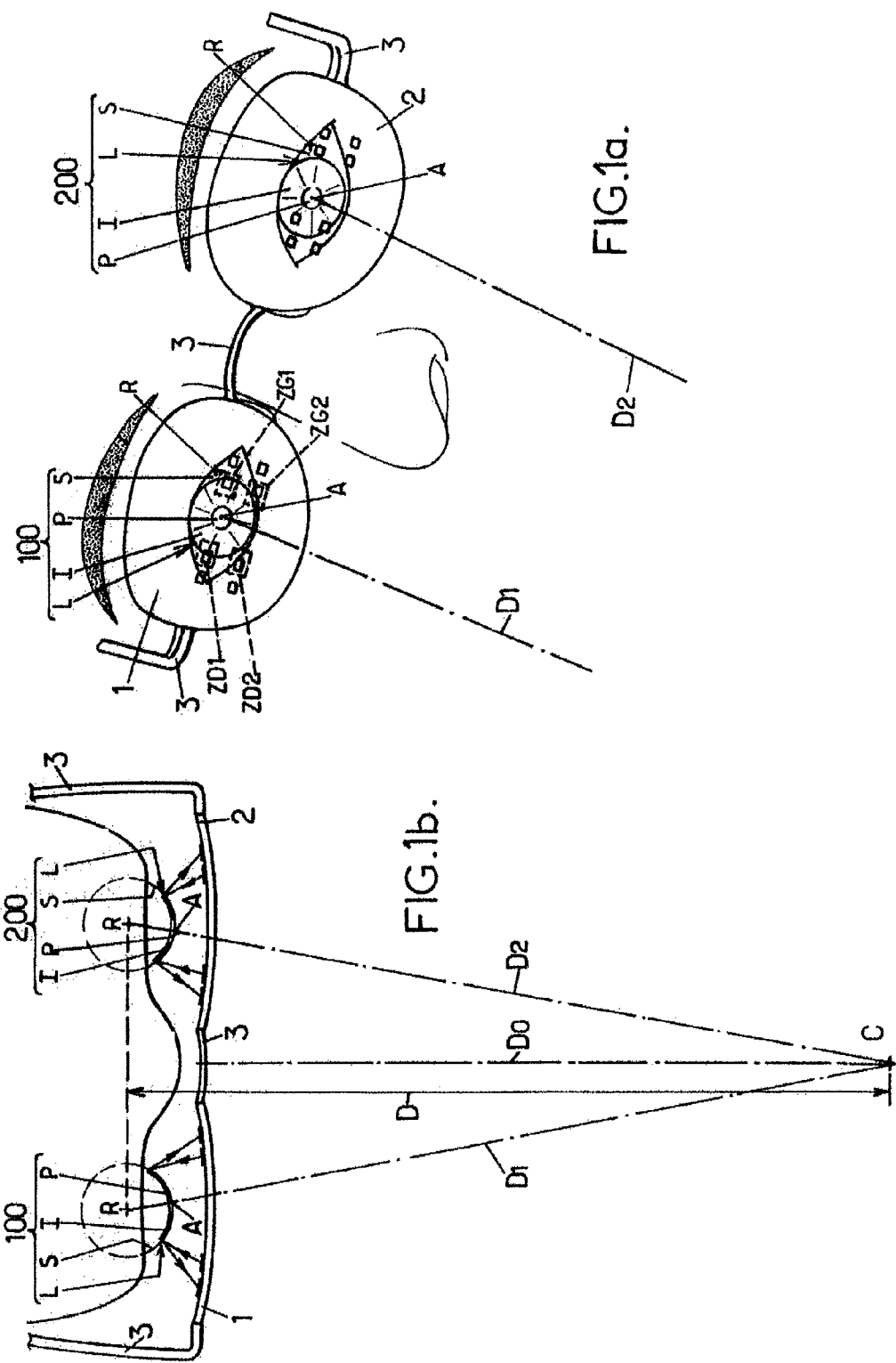

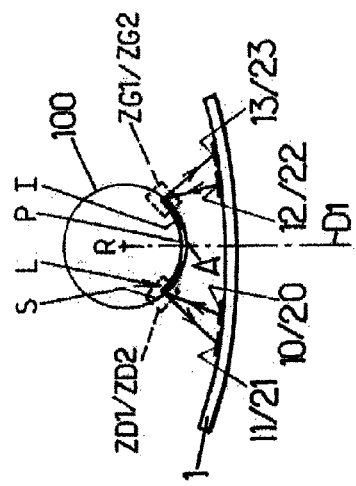
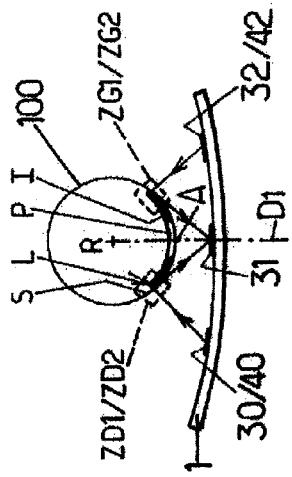
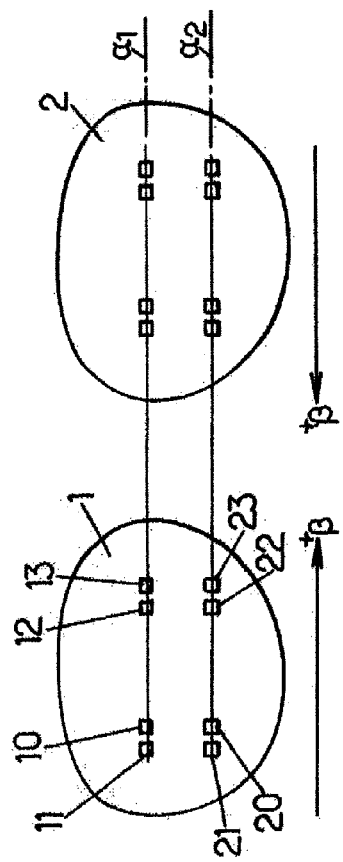
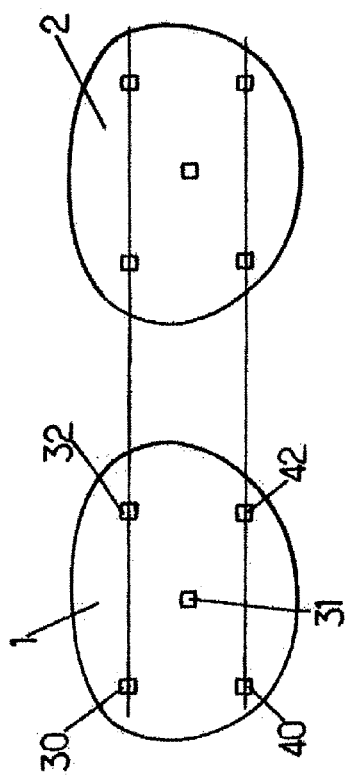

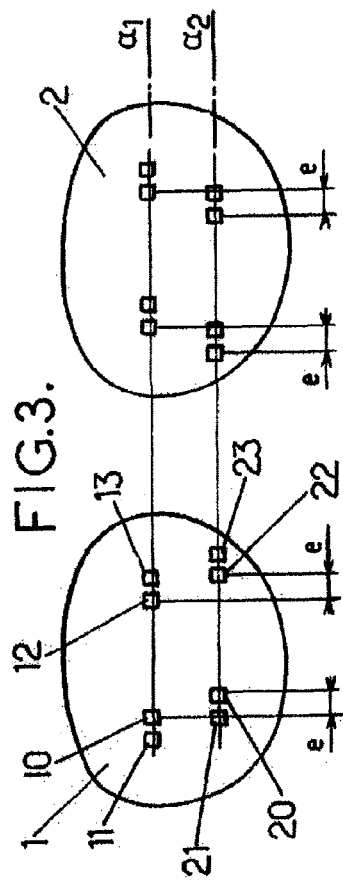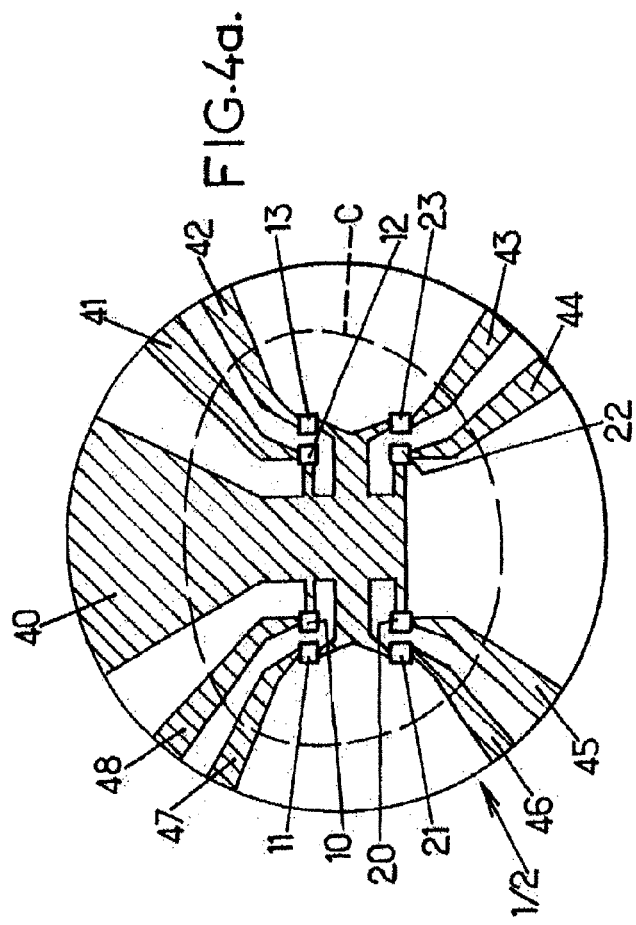

OPHTHALMIC SPECTACLES FOR CHARACTERIZING A CONVERGENCE OF THE EYES OF A WEARER

BACKGROUND

1. Technical Field

The invention relates to a pair of ophthalmic spectacles which is adapted for characterizing a convergence of the eyes of a wearer of the spectacles. It also relates to a lens of such a pair of spectacles.

2. Description of the Related Art

There are many existing systems for detecting the eye movements of a subject in real time. For example, patent U.S. Pat. No. 5,966,197 describes a system for laser ablation eye surgery, which detects and compensates for the eye movements of a patient. This system forms an image of the eye, and its rotational position within the socket is tracked by identifying the position of the limbus in the image. The limbus is the border between the sclera and the iris of the eye, and it can easily be detected in an image of the eye in near infrared light at wavelengths between 900 nm (nanometers) and 1200 nm. The sclera has a high light reflection coefficient of about 90% in this spectral domain, while the iris has a lower reflection coefficient of about 40%.

Other systems for detecting eye movements also exist, intended for use by patients in the conscious state. Some of these other systems consist of devices to be placed on the subject's head, and form images of the two eyes while the subject is looking at objects in his environment. Although a subject wearing one of these devices can remain mobile, these devices are not usable in everyday life but are to limited to use in sessions in which measurements of the subject are collected.

Certain applications require eye movement detection systems which are compatible with mobile use. There is therefore a need for an eye movement detection system which is both light and aesthetically pleasing, and which is not uncomfortable for the subject during prolonged use in everyday life. In addition, such a system is preferably low in cost to allow equipping a large number of individuals. There are currently no such eye movement detection systems in existence which meet these requirements in a satisfactory manner.

BRIEF SUMMARY

One aim of the present invention is to provide an eye movement detection system which is compatible with mobile use in everyday life.

Another aim of the invention is to provide a real-time characterization of the distance of an object observed by a user of the eye movement detection system.

Yet another aim of the invention is to provide a characterization of the convergence of the eyes of the user, and of his eye movements which determine the variations in this convergence.

To achieve this, the invention proposes a pair of ophthalmic spectacles which comprises a frame and two lenses held in the frame so that they are respectively positioned in front of the eyes of a wearer of the spectacles, and which allows separate vision for the wearer through each lens, the pair of spectacles comprising for each lens:

at least one radiation source, which can be infrared radiation, selected so that the radiation is reflected by the sclera and iris of each eye of the wearer in accordance with different reflection intensity coefficients respectively for the sclera and the iris;

at least one detector, which is arranged to measure respective intensities of portions of the radiation produced by the source, respectively reflected in ocular areas in each of which a right or left portion, of a border between the sclera and iris of the eye positioned behind the lens, moves about during eye movements; and at least four radiation output or input sections which are arranged in the lens, each output section being arranged to direct a portion of the radiation produced by the source towards at least one of the ocular areas in which the right and left portions of the border between the sclera and the iris move about, and each input section being arranged to collect a portion of the radiation reflected in one of these ocular areas.

In a first characteristic of the invention, these source(s), detector(s), and radiation output and input sections are additionally arranged so as to form at least four radiation paths which each comprise a reflection on the wearer's eye positioned behind the lens, in one of the ocular areas in which the right and left portions, for their respective paths, of the border between the sclera and the iris of the eye move about. The pair of spectacles then comprises a means for separating the portions of radiation transmitted between said at least one radiation source and said at least one detector by different respective radiation paths.

In a second characteristic of the invention, the pair of spectacles also comprises a computation unit which is adapted for characterizing a convergence of the eyes of the wearer at a common observation point, as a function of the intensities which are simultaneously measured for the two lenses.

In a third characteristic of the invention, said at least one source, said at least one detector, and said at least four radiation output and input areas are arranged in a manner that forms at least two pairs of distinct paths for the radiation, with two first radiation output sections which are arranged in each lens at a same first elevation, and two second radiation output sections which are arranged in each lens at a same second elevation, different from the first elevation. In addition, they are arranged so that the ocular areas in which the right and left portions, for the respective paths of each pair, of the border between the sclera and the iris of the wearer's eye positioned behind the lens, are positioned at a same ocular area elevation which is associated with this pair, and so that the two pairs of paths are associated with respective ocular area elevations which are distinct and common to the two lenses. The computation unit is then adapted to characterize the convergence of the eyes of the wearer as a function of the intensities measured simultaneously for the portions of radiation transmitted by the paths associated with a same ocular area elevation, this elevation being selected by the computation unit for the two lenses.

In this manner, the invention provides a system for detecting a subject's eye movements which is in the form of a pair of spectacles, with radiation input and output sections which are integrated into the lenses. The system is therefore light and very compact because it is in the form of spectacles. It can be used in everyday life, even when the user is moving about. In particular, a person wearing a pair of spectacles of the invention retains complete freedom of movement.

In addition, given that the radiation input and output sections are integrated into each lens, the pair of spectacles is without any supplemental reflector or any image acquisition system directed towards the wearer's eyes, which would be positioned in front of his face in addition to the lenses of the spectacles. An eye movement detection system of the invention is therefore aesthetically pleasing on the wearer's face, and causes him no visual discomfort.

In addition, the detection of eye movements which occurs when using a pair of spectacles of the invention is based on the detection of the positions of right and left portions of the limbus of each eye. To do this, at least four radiation beams are directed from each lens towards the areas of movement of the right and left portions of the limbus of the wearer's corresponding eye, and the respective intensities of these beams are measured after their reflection on each eye in these areas. Each beam has a different radiation path. Its intensity after reflection, when it passes back through one of the input sections of the lens, varies as a function of the rotational position of the eyes because each beam is reflected to a greater or lesser extent depending on whether it reaches the sclera or the iris on the surface of the eye. The convergence of the eyes of the wearer towards a point he is regarding at a given moment is then determined from a comparison between the positions of the limbi of both eyes. In this manner, the convergence of the eyes of the wearer can be determined regardless of the directional angle of an object viewed by the wearer, from his face in a horizontal plane. A characterization of the distance of an object observed by the wearer of the pair of spectacles can then be deduced in real time from the determined convergence of his eyes.

By pairing the radiation output sections within each lens as a function of the elevation of the ocular areas in which the radiation is reflected, the invention allows determining the convergence of the eyes of the wearer for any directional angle of the regarded object relative to the face of the wearer in a vertical plane, called the level of gaze. The paths of the two lenses associated with the same ocular area elevation are used to determine the convergence of the wearer's eyes at a given moment.

In various embodiments of the invention, some the following improvements can be used separately or in combination:
  the computation unit can be adapted to select one of the ocular area elevations for characterizing the convergence of the eyes of the wearer, as a function of a value of a signal-to-noise ratio for at least some of the intensities measured;
  the pair of spectacles can comprise as many radiation output sections as radiation input sections for each lens, each of said output sections being adjacent in the lens to one of said input sections to form a separate radiation emission-reception pair, each emission-reception pair being arranged in front of one of the ocular areas in which one of the right and left portions, of the border between the sclera and the iris of the wearer's eye positioned behind this lens, moves about during eye movements;
  for each lens, the radiation output sections can be arranged in the form of two columns which are respectively positioned in the right and left portions of this lens, with each output section of the column positioned in the right portion of the lens belonging to a radiation path which comprises a reflection on the wearer's eye in the ocular area in which the right portion of the border between the sclera and the iris of this eye moves about, and each output section of the column positioned in the left portion of the lens belonging to a radiation path which comprises a reflection on the wearer's eye in the ocular area in which the left portion of the border between the sclera and the iris of the eye moves about; and
  the source(s), the output section(s), the input section(s), and the detector(s) which are associated with at least one of the lenses can be arranged such that at least two different radiation paths traversing different output sections enter a same input section common to these paths, and the means for separating the portions of radiation as a function of the radiation paths can be adapted to synchronize the measurements made by the detector(s) in accordance with different modulations which are applied to the radiation transmitted by the different paths.

It is possible for a pair of spectacles of the invention to additionally comprise a means for varying a characteristic of at least one of the lenses, as a function of a result for the convergence of the wearer's eyes which is characterized by the computation unit. In particular, the means for varying the characteristic of one of the lenses can be comprised within this lens. For example, each lens can be a single vision lens with an optical power which is adjustable to the observation distance deduced from the convergence of the eyes of the wearer. A presbyopic wearer can thus have visual correction adjusted for each observation distance over the entire surface of the lenses, without residual astigmatism.

A pair of spectacles of the invention can also advantageously be used in orthoptics, during vision reeducation sessions. Such spectacles allow a patient wearing the spectacles to be given more customized and controlled reeducation exercises.

The invention also proposes a spectacle lens adapted for assembly in a pair of spectacles as described above. Such a lens comprises:
  at least one radiation source, which can be infrared radiation, each source being integrated into the lens and selected so that the radiation is reflected by the sclera and iris of an eye of the wearer of the lens, in accordance with different reflection intensity coefficients respectively for the sclera and the iris;
  at least one detector of this radiation, each detector being integrated into the lens and arranged to measure an intensity of a portion of the radiation produced by one of the sources, which is reflected by the eye in an ocular area in which a right or left portion of a border between the sclera and the iris of the eye moves about during eye movements;
  transparent conductive strips, which are integrated into the lens and which electrically connect the terminals of each detector and each source, and which are arranged radially in a peripheral portion of the lens; and
  at least four radiation output or input sections which are arranged in the lens to form radiation paths with the eye of the wearer of this spectacle lens as described above.

The radial arrangement of the conductive strips in the peripheral portion of the lens provides electrical contacts in the frame at determined locations, for establishing electrical connections between the strips of the lens and other electronic components carried by the frame. In addition, this radial arrangement allows the lens to be trimmed to any shape of rim of the frame while retaining the possibility of providing electrical contacts for the frame.

BRIEF DESCRIPTION OF THE SEVERAL VIEWS OF THE DRAWINGS

Other features and advantages of the invention will be apparent from the following description of some non-limiting examples with reference to the attached drawings, in which:
FIGS. 1a and 1b are a perspective view and a plan view showing the use of a pair of spectacles according to a first embodiment of the invention;

FIGS. 2a and 2b are an enlarged front and plan views illustrating the first embodiment of the invention;

FIG. 3 corresponds to FIG. 2a for a second embodiment of the invention;

FIGS. 4a and 4b are a plan view and a cross-sectional view of a lens of the invention;

FIGS. 7a to 7d respectively correspond to FIGS. 2a to 2d for a third embodiment of the invention.

DETAILED DESCRIPTION

Figure 2C:
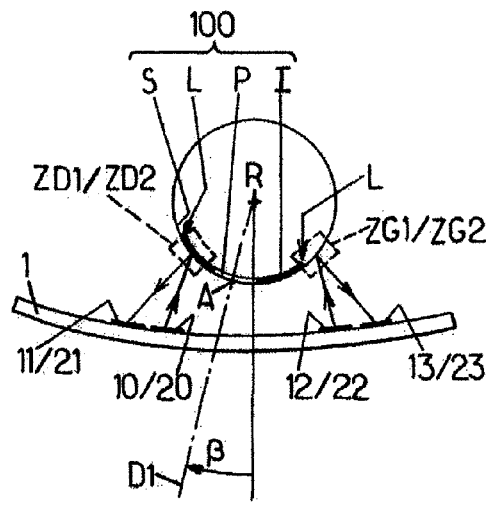
FIGS. 2c and 2d correspond to FIG. 2b, for two different positions of an eye of a person wearing the spectacles.

For clarity, the dimensions of the elements represented in these figures are not in proportion to the actual dimensions, nor to the ratios of the actual dimensions. In addition, use of the same references in different figures denotes identical elements or elements with identical functions.

In FIGS. 1a and 1b, a pair of spectacles comprises a frame 3 and two ophthalmic lenses, respectively denoted 1 and 2 for the right and left lens. The frame 3 holds the lenses 1 and 2 in relative fixed positions, and allows placing them in front of the eyes of the wearer in a manner which remains constant during successive periods of use. The lenses 1 and 2 can be permanently assembled into the frame 3 using one of the assembly methods known to opticians. Alternatively, the lenses 1 and 2 can be added by the invention to an initial pair of spectacles which comprises the frame 3. The initial pair of spectacles can be a pair of spectacles providing solar protection and/or ophthalmic correction. In this case, the lenses 1 and 2 can be placed on the initial pair of spectacles in a removable manner, for example using a clip-on arrangement.

The references 100 and 200 denote the wearer's eyes, 100 indicating the right eye and 200 indicating the left eye. For each of the wearer's eyes 100, 200, the references S, I, P, L and R denote the sclera, the iris, the pupil, the limbus, and the center of rotation of the eye. It is known that the iris I is a circular ring having an inner diameter which is variable and which determines the size of the pupil P, and a constant outer diameter. The limbus L is the outside border of the iris I, between the iris and the sclera S. It is therefore a circle of constant size which is fixed relative to the corresponding eye when the eye is turning around its center of rotation R. Visually, the limbus L is the circular border between the white sclera S and the colored iris I.

For each eye 100, 200, the respective axis D1, D2 which passes through the center of rotation R and the center A of the corresponding pupil P is the optical axis of that eye. The center A of the pupil P is also the apex of the crystalline lens. The optical axis D1, D2, is fixed relative to the respective eye 100, 200, such that it rotates with the limbus L. The optical axes D1 and D2 of the eyes 100 and 200 converge at a common point C (FIG. 1b), which is called the point of convergence of the eyes and which is the location of an object being viewed by the wearer at a given moment. The average direction D0 of the optical axes D1 and D2 is the direction of gaze of the wearer at that moment. Usually, the direction of gaze D0 connects a midpoint of the segment between the two eyes' centers of rotation R and the point of convergence C. The observation distance, which is denoted D in FIG. 1b, is the distance of the point of convergence C relative to the centers of rotation R.

The invention, which is now described in specific embodiments, allows determining the position of the point of convergence C relative to the face of the wearer. In these embodiments, this position of the point C is determined by detecting the rotational position of each eye 100, 200 relative to the corresponding lens 1, 2. Thus each lens 1, 2 of the invention allows determining the angular position of the optical axis D1, D2 of the corresponding eye 100, 200. The point of convergence C, with the observation distance D if necessary, is then deduced from the respective positions of the two optical axes D1 and D2.

To define the position of the optical axis of each eye, two angles are used, $\alpha$ and $\beta$, respectively called the elevation and eccentricity. The elevation $\alpha$ is usually identical for both eyes 100 and 200, and is the angle between each optical axis D1 or D2 and a reference plane which is horizontal when the wearer's head is vertical. The eccentricity $\beta$ of the optical axis D1 or D2 of each eye is the angle between this axis and a median plane of the face, which is vertical when the wearer's head is vertical. The eccentricity $\beta$ generally has distinct values for the two eyes at the same moment, and the difference between these two values determines the convergence of the eyes, meaning the observation distance D.

In practice, the eccentricity of the optical axis D1, D2 of each eye 100, 200 is determined based on the position of the limbus L of that eye. More specifically, the respective positions of the right and left edges of the limbus L are determined by measuring the intensities of the radiation reflected by the eye in right and left lateral areas of said eye. To do this, each lens is provided with radiation emission sections, called output sections, which direct one or more radiation beams towards the lateral areas of the eye in which the right and left portions of the limbus move about when the eye rotates. It is also equipped with collection sections, called input sections, for collecting portions of this radiation reflected in the lateral areas of the eye. The output sections are supplied with radiation by at least one radiation source, and the input sections are optically connected to at least one detector in order to measure the intensities of the respective portions of radiation collected by these input sections.

Figure 2D:
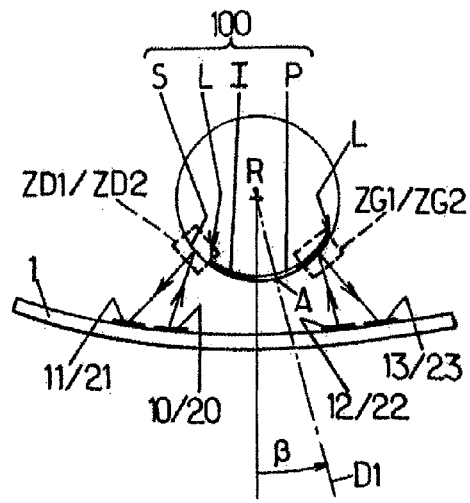

In the right lens 1 in FIGS. 2a to 2d, a first emission-reception pair consists of the output section 10 and the input section 11. The sections 10 and 11 are adjacent, for example in a horizontal direction, with a space between them which can be between 0.1 and 3 mm (millimeters). A second emission-reception pair consists of another output section 12 and another input section 13. The pairs 10/11 and 12/13 can be identical in composition. They are positioned in the lens 1 at equal values for the elevation $\alpha$, denoted $\alpha_1$. They are also positioned at different eccentricity values $\beta$: the emission-reception pair 10/11 is positioned facing the right lateral area ZD1 of the eye where the right portion of the limbus L moves about, and the emission-reception pair 12/13 is positioned facing the left lateral area ZG1 of the eye where the left portion of the limbus L moves about. Each emission-reception pair therefore determines a radiation path which is indicated in FIGS. 2b to 2d, from the corresponding output section 10 or 12 to the corresponding input section 11 or 13, and which comprises a point in the corresponding area ZD1 or ZG1 where the radiation is reflected. In such an embodiment of the invention, the different radiation paths used to determine the rotational position of the eye are therefore separated by the manner in which the radiation output and input sections are arranged in the lens.

FIGS. 2b, 2c and 2d respectively represent rotational positions of the right eye 100, in which the optical axis D1 corresponds to an eccentricity value $\beta$ which is zero (FIG. 2b), negative or oriented towards the temporal side (FIG. 2c), and positive or oriented towards the nasal side (FIG. 2d). When the wavelength of the radiation used is between 900 and 1200 nm, the difference between the reflection intensity from the iris, which is low, and from the sclera, which is higher, allows detecting the position of the eye 100. Thus the reflections detected in the lateral areas ZD1 and ZG1 by the respective emission-reception pairs 10/11 and 12/13 have intensities which are substantially identical in the case in FIG. 2b, while the intensity for the pair 10/11 is less than for 12/13 in the case of FIG. 2c and is greater in the case of FIG. 2d. When the eccentricity β of the optical axis D1 continuously varies, the intensities measured for the portions of radiation which reach the input sections 11 and 13 also vary continuously, in opposite directions. The emission-reception pairs 10/11 and 12/13 therefore allow determining the angular position of the optical axis D1 of the eye 100, in a horizontal plane when the head of the wearer is vertical.

It is possible for the wearer to be fitted with contact lenses which improve the position detection sensitivity for each eye. Such a contact lens can cover the iris of the corresponding eye while remaining centered on its optical axis for any rotational position of the eye. It can then be designed to adapt the value of the apparent reflection coefficient of the iris in order to increase the reflection contrast between the iris and the sclera.

A computation unit is associated with the pair of spectacles. It can be incorporated into one of the arms of the frame 3, for example. Such a computation unit is adapted to determine the angular position of the optical axis D1 from the measured intensities of the reflected portions of radiation. This determination of the angular position of the optical axis D1 can be done by computation. Alternatively, the computation unit can determine the angular position of the optical axis D1 by reading from a stored table which indicates this position as a function of intensity values measured for the different radiation paths, used as inputs to this table.

It is understood that the left lens 2 has a configuration which is analogous to that of the right lens 1, being symmetrical to the right lens relative to the median plane of the wearer's face. The computation unit then allows determining the angular position of the optical axis D2 of the wearer's left eye 200, at the same times as the positions are determined for the optical axis D1 of the right eye 100. The observation distance D is then obtained, possibly as well as the position of the center of convergence C of the two eyes and/or the direction of gaze D0.

As has just been described, the computation unit can be adapted for first determining an angular position of the optical axis of each eye based on intensities which are simultaneously measured for the lens positioned in front of that eye, and for the portions of radiation reflected in certain of the ocular areas in which the right and left portions of the border between the sclera and iris of the eye move about. The computation unit is also adapted for then determining the convergence of the eyes of the wearer based on the respective angular positions of the optical axes of the two eyes which were determined for the same moment in time. However, such an operation of the computation unit in two successive steps is not indispensable. The convergence of the eyes of the wearer, possibly with the angular position of the direction D0 and the observation distance D, can be deduced in a single step based on (an) appropriate combination(s) of intensities simultaneously measured for the portions of radiation reflected in the lateral areas of the two eyes in which the corresponding right and left portions of limbi L move about.

Each lens is additionally arranged to determine at least two pairs of radiation paths, which comprise reflections on the eye of the wearer in lateral areas which are positioned at a same first elevation $\alpha_1$ for the paths of a same first pair, and at a same second elevation $\alpha_2$ for the paths of a same second pair. FIGS. 2a to 2d illustrate such an improved embodiment when each path is determined by an emission-reception pair separate from those of the other paths. Thus, the output section 10 with the input section 11, and the output section 12 with the input section 13, determine a first pair of radiation paths which are positioned at the elevation value $\alpha_1$. Similarly, the output section 20 with the input section 21, and the output section 22 with the input section 23, determine a second pair of radiation paths which are positioned at the elevation value $\alpha_2$. The emission-reception pair 20/21 determines a supplemental optical path which comprises a point of reflection on the eye 100 which is positioned in a right lateral area ZD2 of the eye at elevation $\alpha_2$ below the area ZD1. Similarly, the emission-reception pair 22/23 determines another supplemental optical path which comprises a point of reflection on the eye 100 which is positioned in a left lateral area ZG2 of the eye at elevation $\alpha_2$ below the area ZG1. In this case, the elevations of the ocular areas which are associated with the two pairs of radiation paths can have a difference of between 10° and 45° in their absolute value. Thus one of these elevation values, for example $\alpha_1$, can correspond to viewing an object which is substantially situated at the wearer's eye level. The other elevation value, $\alpha_2$, can correspond to viewing an object situated in the lower portion of the wearer's field of vision. The computation unit can then be adapted to select one of the ocular area elevation values for characterizing the convergence of the eyes of the wearer. Such a selection can be done, in particular, as a function of a value of a signal-to-noise ratio for at least some of the intensities measured. In this manner, the radiation paths which can be obscured by the lowering of the wearer's eyelids are not taken into account when determining the convergence of his eyes.

FIG. 3 illustrates an improvement of the invention, in which the emission-reception pairs corresponding to one of the elevation values are laterally offset relative to the emission-reception pairs which correspond to the other elevation value. Thus the emission-reception pairs 20/21 and 22/23 which define reflections on the eye at the elevation $\alpha_2$ are offset towards the nasal side by a distance e relative to the emission-reception pairs 10/11 and 12/13 which define reflections on the eye at the elevation $\alpha_1$. When the lenses 1 and 2 are lenses with progressive addition of optical power, commonly referred to as progressive lenses, the elevation values $\alpha_1$ and $\alpha_2$ can respectively correspond to the elevations in each lens for the directions of near and far vision. The offset e can then be substantially equal to the offset which results from the variable convergence of the eyes between the conditions of near and far vision, and which is commonly referred to as inset. In this case, the offset e can be between 4 and 6.5 mm. More generally, it can be between 0 and 7 mm.

In a first type of embodiment of the invention, each radiation source can be a light emitting diode which operates at a wavelength of between 900 nm and 1200 nm. In this case, each radiation output section corresponds to a portion of the emitting surface of this diode. Alternatively, each radiation source can be a VCSEL source (Vertical Cavity Surface Emitting Laser).

In parallel, each detector can be a photodiode or a phototransistor. Each radiation input section then corresponds to a photosensitive portion of the surface of the photodiode or phototransistor.

In a particularly advantageous combination, each radiation source and each detector are micro-optoelectronic components based on semiconductor materials, which are integrated into each lens. In this manner, each lens is an autonomous element which is adapted to implement the invention at a production and frame assembly cost which can be very low. In this case, each lens additionally comprises transparent conductive strips which electrically connect the terminals of each source and of each detector. These strips connect the sources and detectors to the computation unit which can be external to the spectacle lens. Preferably, the conductive strips are arranged radially in a peripheral portion of the lens. Due to such an arrangement of the strips, the lens can be trimmed to the shape of the rim of the frame 3, while easily identifying where each of the conductive strips emerge at the trimmed edge. For example, the conductive strips occupy separate angular sectors in the peripheral portion of the lens. As shown in FIGS. 4*a* and 4*b*, each lens 1, 2 can comprise a base part 50 and an encapsulation part 51 which are integrally attached, and each radiation source, each detector, and each conductive strip can be placed between the parts 50 and 51. For example, the strip 40 can constitute a ground terminal shared by all radiation sources and detectors of the lens, and the strips 41 to 48 respectively connect another terminal of each of the sources 10, 12, 20, 22 and each of the detectors 11, 13, 21, 23. These strips, sources, and detectors can be formed on the base part 50 and be coated in a transparent layer of glue 52 which establishes the mechanical bond to the encapsulation portion 51. The radiation sources and detectors advantageously have very small dimensions, to avoid interfering with the vision of the wearer and be invisible. In addition, the strips 40-48 can consist of any material which is both transparent and electrically conductive, such as tin-doped indium oxide or ITO (indium-tin oxide). Alternatively, each strip 40-48 can be replaced with a very thin conductive wire, arranged radially in the peripheral portion of the lens. In FIG. 4*a*, C denotes a trim line which is indicated as an example. The trim line C cuts through each of the strips 40-48 in a radially arranged portion.

Figure 5:
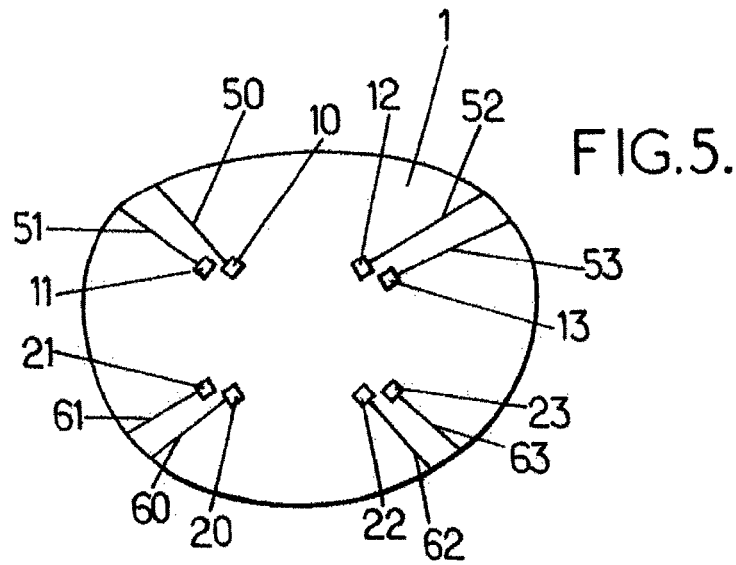
FIGS. 5 and 6 illustrates two different types of embodiments of the invention.

In a second type of embodiment of the invention, each radiation source can be located externally to the corresponding lens and can be optically coupled to one of the output sections by a first optical guide, for example an optical fiber. Similarly, each radiation detector can also be located externally to the lens and can also be optically coupled to one of the radiation input sections by a second optical guide, which can be separate from or combined with one of the first optical guides. In a particular lens manufacturing method, each first or second optical guide can be incorporated into the lens during its molding, by placing it in an injection mold before the material constituting the lens is introduced into the mold. It is possible for each radiation output or input section to have a microprism integrated into the lens, which determines the direction the radiation is emitted towards a lateral area of the eye, or the direction the reflected portion of the radiation is collected. In other words, each radiation output or input section is formed by a face of a microprism positioned at the end of an optical guide. In FIG. 5, the references 50-53 and 60-63 denote optical fibers which respectively connect the output and input sections 10-13 and 20-23. For the same reason as above concerning conductive strips, the optical fibers 50-53 and 60-63 are preferably arranged radially in the lens 1, so their positions at the trim line C are easily determined.

Figure 6:
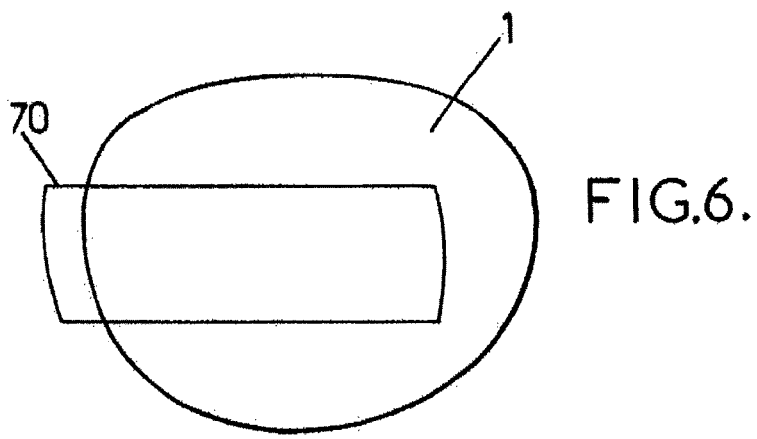

In a third type of embodiment of the invention, the pair of spectacles may additionally comprise an optical guide for each lens, which forms an image of a portion of the eye externally to this lens. In FIG. 6, the reference 70 denotes such an optical guide, embodiments of which will be known to a person skilled in the art and will therefore not be described here. In an advantageous configuration, the optical guide 70 penetrates the lens 1 from the temporal edge of the lens, at the arm of the frame 3, to avoid reducing the usability and appearance of the lens. It is possible for the optical guide to also bring the radiation from a source external to the lens, to produce sufficient light intensity for detecting the image of the eye. It then delivers the radiation from the source through at least four zones of the optical guide 70, which form the radiation output sections. Advantageously, an active face of the optical guide 70 positioned facing the eye is continuous between the output sections. The detectors are then distributed in areas of the image of the eye, imaged by the optical guide, in which the right and left portions of the border between the sclera and iris of the eye move about during eye movements.

FIGS. 7*a* to 7*d* illustrate another embodiment of a lens of the invention, in which several optical paths comprising respective points of reflection in the lateral areas ZD1, ZD2, ZG1 and ZG2 of the eye, have the same radiation input section in common. In these figures, the references 30 and 32 denote the radiation output sections positioned at a same first elevation in the lens, references 40 and 42 denote the radiation, output sections positioned at a same second elevation in the lens, and the reference 31 denotes the input section which is common to the four output sections. The first radiation path therefore issues from output section 30, comprises a reflection in the lateral ocular area ZD1 in which the upper right portion of the limbus L moves about, and arrives at the input section 31. The second radiation path issues from the output section 32, comprises a reflection in the lateral ocular area ZG1 in which the upper left portion of the limbus L moves about, and also arrives at the input section 31. Similarly, the third radiation path issues from the output section 40, comprises a reflection in the lateral ocular area ZD2 in which the lower right portion of the limbus L moves about, and also arrives at the input section 31. Lastly, the fourth radiation path issues from the output section 42, comprises a reflection in a lateral ocular area ZG2 in which the left lower portion of the limbus L moves about, and also arrives at the input section 31. In this case, the outputs sections 30, 32, 40, and 42 can each be supplied with radiation in four different temporal modulations, and the detector which is optically connected to the input section 31 is controlled to perform synchronous detection. Such synchronous detection allows separating the portions of radiation which follow one of the four paths passing through one of the ocular areas, although the four paths share the same input section and the same detector. Other means may alternatively be used to separate the portions of radiation which follow one of these paths. For example, different radiation wavelengths or polarizations can be used for each of the paths, and filtering is applied to separate the portions of radiation collected by the common input section which originate from each ocular area.

Figure 7C:
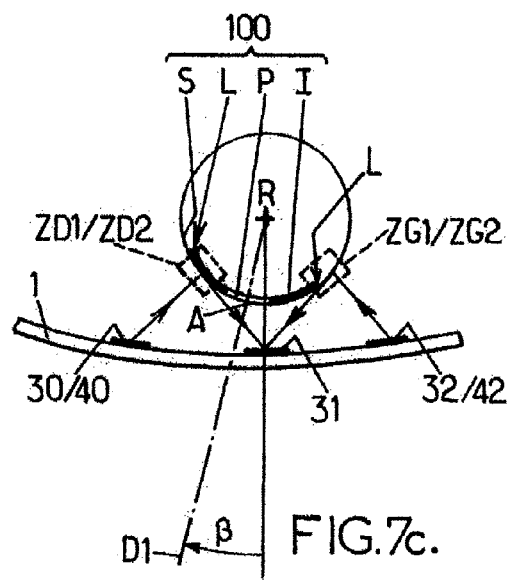
Figure 7D:
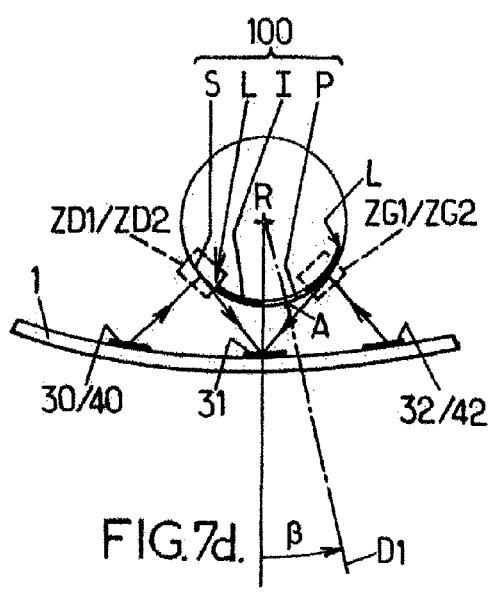

FIGS. 7*c* and 7*d* show different positions of the limbus L of the eye 100, relative to the lateral ocular areas which contain the reflections of the four radiation paths. The intensities of the reflected portions of radiation which follow one of the four paths vary in the same manner as described above for FIGS. 2*c* and 2*d*.

In yet another embodiment of a lens of the invention, several paths which comprise respective points of reflection in the lateral areas of the eye can have a same radiation output section in common, and possibly a same radiation source. They then arrive at radiation input sections which are different. Such an embodiment is simple to deduce from the above and is therefore not described.

The last two embodiments described above simplify the production of the spectacle lenses, as they then comprise a reduced number of components.

Figure 8:
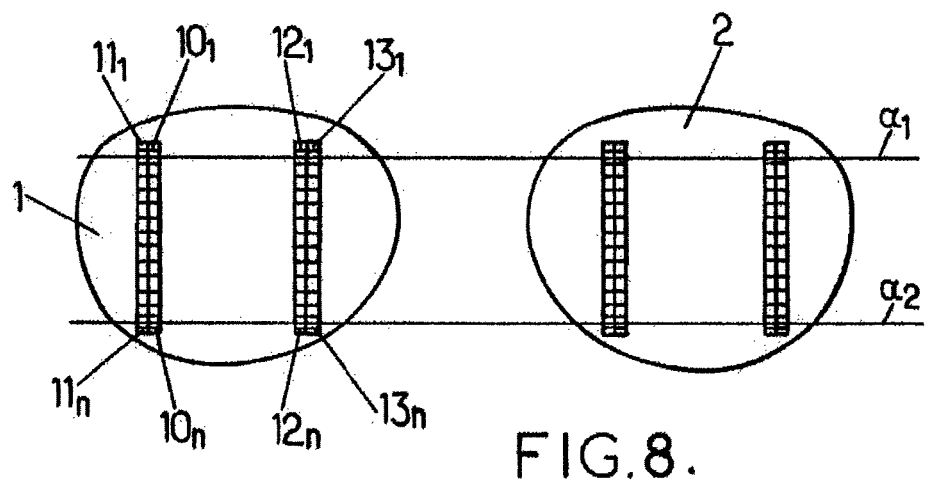
FIG. 8 corresponds to FIG. 3 for a fourth embodiment of the invention.

Lastly, FIG. 8 illustrates yet another embodiment of the invention, which is deduced from the one in FIGS. 2a to 2d. The two radiation output sections and the two radiation input sections are replaced, in the right and left portions of each spectacle lens, with respective columns of output sections and columns of input sections. Thus the right portion of the lens 1 contains a column of output sections $10_1, \ldots, 10_n$, where n is a natural number greater than 2, and a column of input sections $11_1, \ldots, 11_n$. These two columns are vertical relative to the utilization position of the lens 1 for the wearer, are parallel, and are preferably close to each other, with output and input sections which are progressively offset towards the bottom of the lens at identical elevation decrements. However, it is not necessary for the sections within the same column to be contiguous, such that they can be paired off by intervals. The left portion of the lens 1 contains a column of output sections $12_1, \ldots, 12_n$ and a column of input sections $13_1, \ldots, 13_n$ which can be analogous to those in the right portion of the same lens 1. The lens 2 has a structure symmetrical to that of the lens 1. It is possible for these columns of output or input sections to be directly formed by columns of sources, such as infrared light emitting diodes for example, or by columns of detectors, such as photodiodes or phototransistors for example.

The use of such source columns or detector columns is particularly advantageous for characterizing the convergence of the eyes of the wearer without requiring the use of too much power. The energy source which powers the sources, detectors, and computation unit can then be of reduced capacity. In fact, the sources and detectors which correspond to radiation paths having reflections on the eye at the same ocular area elevation, can be selected in accordance with one of the following strategies, while the other sources and detectors are not activated:

/i/ the sources and detectors can be activated sequentially, in a scanning order which is predetermined;

/ii/ the sources and detectors activated for a new sequence of measuring the intensity of the radiation reflected from the eye can be selected as a function of at least one value of a signal-to-noise ratio obtained during a prior measurement sequence;

/iii/ they can be selected as a function of a predictive algorithm concerning the elevation of the reflection from the eye which is most suitable for recharacterizing the convergence of the wearer's gaze, as a function of the elevations already selected during prior characterizations. This strategy can take into account a previously determined elevation of the direction of gaze; and /iv/ a composite strategy which combines the selection criteria of strategies /i/ to /iii/ above.

These strategies are particularly suitable for preventing movements of the wearer's eyelids from interfering with the characterization of the convergence of his gaze according to the invention.

A person skilled in the art will understand that the invention is not limited to the particular embodiments described in relation to the figures. In particular, the different types of embodiments of the invention which have been listed can be combined in multiple ways with different positions and routes for the radiation paths, these paths comprising respective points of reflection in the lateral areas of the eye in which the right and left portions of the limbus move about. In addition, the positions of the radiation output and input sections within each lens can be freely modified, to form radiation paths which comprise points of reflection located within variable areas on the eye. It is possible for the same section in which radiation passes through the lens to be both a radiation output section and a radiation input section. In this case, this section is substantially positioned in the direction perpendicular to the surface of the eye in the corresponding ocular area.

In particular, in an embodiment in which the output and input sections which are part of the same emission-reception pair are adjacent to each other, the relative positions of the output section and the input sections can be modified while maintaining a point of reflection of the corresponding radiation path which remains at the same location on the eye. In particular, the positions of the output section and input section can be exchanged.

Various improvements to the invention are now described, which increase the reliability of the determination of the convergence of the eyes, and/or which improve the comfort and/or safety of the person wearing the pair of spectacles.

In a first of these improvements, the pair of spectacles can additionally comprise a means for modulating the radiation produced by each source, and a means for processing the detection signal produced by each detector. These means are adapted to perform a synchronous detection of each portion of the radiation which is reflected from the eye of the wearer, based on the modulation of the source. In particular, such a synchronous detection allows distinguishing the radiation produced for the invention, from any background ambient radiation. In particular, the modulation can be selected so that the synchronous detection effectively eliminates contributions from ambient radiation at frequencies which are multiples of 50 Hz (Hertz). Such contributions are commonly produced by discharge lighting systems.

In a second improvement, the pair of spectacles can additionally comprise a means for filtering a measurement signal produced by each detector. This means can be adapted to delete measurements which correspond to involuntary variations in the convergence of the eyes of the wearer. Involuntary variations in the convergence of the eyes of the wearer are generally much more rapid than variations resulting from voluntary changes between objects successively regarded by the wearer. In this manner, the determination of the convergence of the eyes of the wearer can be limited to changes in visual attention of which the wearer is aware. Thus, when the invention is used to control a variable characteristic of the lenses, this characteristic is only modified during a measurement that is useful relative to the visual attention of the wearer.

Lastly, in a third improvement, the pair of spectacles can also comprise a means for controlling each radiation source, which is adapted to activate an intermittent operation of this source in accordance with a duty cycle of between 2% and 50%, and preferably less than 10%. The value of this duty cycle can be selected based on several different criteria, including a limitation of the amount of radiation directed towards the eye and a limitation of the electrical power consumed by a spectacle lens of the invention. In fact, such a lens is preferably supplied with electricity from a battery housed in the frame. Also, the source can be activated to perform two successive determinations of the convergence of the eyes of the wearer which are separated by a fixed period. Such a waiting period is generally independent of the duty cycle of the sources' operation. In particular, it can be determined as a function of the time required for the computation unit to determine the convergence of the eyes from measurement signals produced by the detectors.

The invention claimed is:

1. A pair of ophthalmic spectacles, comprising:
   two lenses;
   a frame configured to hold and respectively position the two lenses in front of corresponding eyes of a wearer of said spectacles, and allow separate vision for the wearer through each lens, said pair of spectacles including for each lens:
      at least one radiation source configured to produce radiation to be reflected by the sclera and by the iris of the corresponding eye of the wearer in accordance with different reflection intensity coefficients respectively for the sclera and the iris;
      at least one detector configured to measure respective intensities of portions of the radiation produced by the source, respectively reflected in ocular areas, of a border between the sclera and the iris of the corresponding eye, that move about during eye movements, each ocular area being in a left portion or a right portion of the border; and
      at least four radiation output or input sections arranged in the lens, each output section being arranged to direct a portion of the radiation produced by the source towards at least one of said ocular areas, and each input section being arranged to collect a portion of the radiation reflected in one of said ocular areas, so as to form at least four radiation paths which each comprise a reflection on the eye corresponding to said lens, in one of the ocular areas in which the right and left portions, for their respective paths, of the border between the sclera and the iris of said eye move about;
   a means for separating the portions of radiation transmitted between said at least one radiation source and said at least one detector by different respective radiation paths; and
   a computation unit configured to characterize a convergence of the eyes of the wearer at a common observation point, as a function of the intensities which are simultaneously measured for the two lenses, wherein
      for each lens, said at least one source, said at least one detector, and said at least four radiation output sections or input sections are arranged to form at least two pairs of distinct paths for the radiation, with two first radiation output sections arranged in each lens at a same first elevation, and two second radiation output sections arranged in each lens at a second elevation which is different from said first elevation,
      the ocular areas in which the right and left portions, for the respective paths of each pair, of the border between the sclera and the iris of the corresponding eye, are positioned at a same ocular area elevation which is associated with said pair, the two pairs of paths being associated with respective ocular area elevations which are distinct from each other and common to the two lenses, and
      the computation unit is configured to characterize the convergence of the eyes of the wearer as a function of the intensities measured simultaneously for the portions of radiation transmitted by the paths associated with a same ocular area elevation, selected by said computation unit for the two lenses.

2. A pair of spectacles according to claim 1, wherein the computation unit is adapted to select one of the elevations of the ocular areas, for characterizing the convergence of the eyes of the wearer as a function of a value of a signal-to-noise ratio for at least some of the intensities measured.

3. A pair of spectacles according to claim 1, wherein the computation unit is adapted for first determining an angular position of an optical axis of each eye from the intensities measured simultaneously for the lens corresponding to said eye, and for the portions of radiation reflected in some of the ocular areas in which the right and left portions of the border between the sclera and the iris of said eye move about,
   and the computation unit is additionally adapted for then determining the convergence of the eyes of the wearer based on the respective angular positions of the optical axes of the two eyes, determined for the same moment in time.

4. A pair of spectacles according to claim 1, comprising as many radiation output sections as radiation input sections for each lens, each of said output sections being adjacent in the lens to one of said input sections to form a separate radiation emission-reception pair, each emission-reception pair being placed in front of one of the ocular areas in which one of the right and left portions of the border between the sclera of the wearer's eye corresponding to said lens moves about during eye movements.

5. A pair of spectacles according to claim 1, wherein, for each lens, the radiation output sections are arranged in the form of two columns respectively positioned in the right and left portions of said lens, each output section of the column positioned in the right portion of the lens belonging to a radiation path comprising a reflection on the wearer's eye in the ocular area in which the right portion of the border between the sclera of said eye moves about, and each output section of the column positioned in the left portion of the lens belonging to a radiation path comprising a reflection on the wearer's eye in the ocular area in which the left portion of said border between the sclera and the iris of the eye moves about.

6. A pair of spectacles according to claim 1, wherein said at least one source, the output sections, at least one input section, and said at least one detector which are associated with at least one of the lenses, are arranged such that at least two different radiation paths traversing different output sections reach a same input section common to said paths, and the means for separating the portions of radiation as a function of the radiation paths is adapted to synchronize the measurements made by said at least one detector in accordance with different modulations applied to the radiation transmitted by said different paths.

7. A pair of spectacles according to claim 1, wherein each radiation source and each detector are micro-optoelectronic components based on semiconductor materials, integrated into the corresponding lens, and said lens additionally comprises transparent conductive strips electrically connecting terminals of each detector and of each source to the computation unit, and radially arranged in a peripheral portion of the lens.

8. A pair of spectacles according to claim 1, wherein each radiation source is located externally to the corresponding lens and is optically coupled to one of the output sections by a first optical guide, and each detector is located externally to the corresponding lens and is optically coupled to one of the input sections by a second optical guide.

9. A pair of spectacles according to claim 1, additionally comprising an optical guide for each lens, which forms an image of a portion of the eye externally to said lens, and wherein the detectors are distributed in areas of said image in which the imaged right and left portions of the border between the sclera of said eye move about during eye movements.

10. A pair of spectacles according to claim 1, additionally comprising a means for varying a characteristic of at least one of the lenses, as a function of a result of the convergence of the eyes of the wearer which is characterized by the computation unit.

11. A spectacle lens comprising:
- at least one radiation source, each source being integrated into said lens and selected so that said radiation is reflected by a sclera and by an iris of an eye of a wearer of the lens, in accordance with different reflection intensity coefficients respectively for the sclera and the iris;
- at least one detector of said radiation, each detector being integrated into said lens and arranged to measure an intensity of a portion of the radiation produced by one of the sources and reflected by the eye in an ocular area in which a right or left portion of a border between the sclera and the iris of said eye moves about during eye movements;
- transparent conductive strips integrated with said lens, electrically connecting terminals of each detector and of each source, and radially arranged in a peripheral portion of the lens; and
- at least four radiation output or input sections arranged in the lens, each output section being arranged to direct a portion of the radiation produced by the source to at least one of said ocular areas, and each input section being arranged to collect a portion of the radiation reflected in one of said ocular areas;
- so as to form at least two radiation paths each comprising a reflection on the wearer's eye, in one of the ocular areas in which the right and left portions, respectively for their said paths, of the border between the sclera and the iris of said eye move about,
- with two first radiation output sections arranged in the lens at a same first elevation, and two second radiation output sections arranged in said lens at a same second elevation, different from the first elevation.

12. A spectacle lens according to claim 11, comprising as many radiation sources as detectors, each of the sources being adjacent in the lens to one of the detectors to form a separate radiation emission-reception pair, each emission-reception pair being arranged in front of one of the ocular areas in which one of the right and left portions of the border between the sclera of the wearer's eye moves about during eye movements.

13. A spectacle lens according to claim 11, wherein the sources are arranged in the form of two columns respectively positioned in right and left portions of said lens, each source of the column positioned in the right portion of the lens belonging to a radiation path comprising a reflection on the wearer's eye in the ocular area in which the right portion of the border between the sclera of said eye moves about, and each source of the column positioned in the left portion of the lens belonging to a radiation path comprising a reflection on the wearer's eye in the ocular area in which the left portion of said border between the sclera and the iris of the eye moves about.

14. A spectacle lens according to claim 11, wherein each radiation source is a light emitting diode operating at a wavelength of between 900 nm and 1200 nm.

15. A spectacle lens according claim 11, wherein each detector is a photodiode or a phototransistor.

16. A spectacle lens according to claim 11, additionally comprising a base part of the lens and an encapsulation part of the lens, said base and encapsulation parts being integrally attached, and each radiation source, each detector, and each conductive strip of said lens being arranged between said base and encapsulation parts.

17. A spectacle lens according to claim 11, additionally comprising a means for varying a characteristic of said lens.

* * * * *